US006858680B2

United States Patent
Gunatillake et al.

(10) Patent No.: US 6,858,680 B2
(45) Date of Patent: Feb. 22, 2005

(54) SHAPE MEMORY POLYURETHANE OR POLYURETHANE-UREA POLYMERS

(75) Inventors: Pathiraja A. Gunatillake, Mulgrave (AU); Simon J. McCarthy, Portland, OR (US); Gordon F. Meijs, Murrumbeena (AU); Raju Adhikari, Wheelers Hill (AU)

(73) Assignee: Aortech Biomaterials Pty Ltd, Chatswood (AU)

( * ) Notice: Subject to any disclaimer, the term of this patent is extended or adjusted under 35 U.S.C. 154(b) by 0 days.

(21) Appl. No.: 10/054,742

(22) Filed: Jan. 22, 2002

(65) Prior Publication Data

US 2002/0161114 A1 Oct. 31, 2002

Related U.S. Application Data

(63) Continuation of application No. PCT/AU00/00863, filed on Jul. 18, 2000.

(30) Foreign Application Priority Data

Jul. 20, 1999 (AU) .............................................. PQ1707

(51) Int. Cl.[7] .............................................. C08G 77/38
(52) U.S. Cl. ...................... 525/474; 525/477; 525/464; 525/452; 525/937; 528/68; 528/76; 528/85
(58) Field of Search ................................ 525/474, 477, 525/464, 452, 937; 528/68, 76, 85

(56) References Cited

U.S. PATENT DOCUMENTS

| | | | |
|---|---|---|---|
| 4,786,657 A | 11/1988 | Hammar et al. | ............... 522/90 |
| 5,049,591 A | 9/1991 | Hayashi et al. | ............. 521/159 |
| 5,139,832 A | 8/1992 | Hayashi et al. | ............. 42/35.5 |
| 5,393,858 A | 2/1995 | Meijs et al. | ................... 528/61 |
| 5,430,121 A | 7/1995 | Pudleiner et al. | ............. 528/28 |
| 5,814,705 A | 9/1998 | Ward et al. | .................... 525/88 |
| 5,911,737 A | 6/1999 | Lee et al. | .................... 606/209 |

FOREIGN PATENT DOCUMENTS

| | | | |
|---|---|---|---|
| AU | 41924/97 | 4/1998 | ........... C08G/18/08 |
| JP | 63-179916 A | 7/1988 | ........... C08G/18/61 |
| JP | 4-248826 | 9/1992 | ........... C08G/18/83 |
| JP | 7-224138 A | 8/1995 | ........... C08G/18/61 |
| WO | WO-98/13405 | 4/1998 | ........... C08G/18/44 |
| WO | WO-99/03863 | 1/1999 | ............ C07F/7/08 |

Primary Examiner—Kuo-Liang Peng
(74) Attorney, Agent, or Firm—Schwegman, Lundberg, Woessner & Kluth, P.A.

(57) ABSTRACT

A shape memory polyurethane or polyurethane-urea polymer including a reaction product of: (A) (a) silicon-based macrodiol, silicon-based macrodiamine and/or polyether of the formula (I): A—$[(CH_2)_m$—$O]_n$—$(CH_2)_m$—A', wherein A and A are endcapping groups; m is an integer of 6 or more; and n is an integer of 1 or greater; (b) a diisocyanate; and (c) a chain extender; or (B) (b) a diisocyanate: and (c) a chain extender, said polymer having a glass transition temperature which enables the polymer to be formed into a first shape at a temperature higher than the glass transition temperature and maintained in said first shape when the polymer is cooled to a temperature lower than the glass transition temperature, said polymer then being capable of resuming its original shape on heating to a temperature higher than the glass transition temperature. The present invention also relates to a shape memory composition which includes a blend of two or more of the shape memory polyurethane or polyurethane-urea polymers defined above or at least one shape memory polyurethane or polyurethane-urea polymer defined above in combination with another material. The present invention further relates to processes for preparing materials having improved mechanical properties, clarity, processability, biostability and/or degradation resistance and devices or articles containing the shape memory polyurethane or polyurethane-urea polymer and/or composition defined above.

5 Claims, No Drawings

SHAPE MEMORY POLYURETHANE OR POLYURETHANE-UREA POLYMERS

RELATED APPLICATIONS

This is a continuation under 37 C.F.R. 1.53(b) and 35 U.S.C. 111(a) of International Application No. PCT/AU00/00863 filed Jul. 18, 2000 and published in English as WO 01/07499 A1 on Feb. 1, 2001, which claimed priority from Australian Applications No. PQ 1707 filed Jul. 20, 1999, which applications are incorporated herein by reference.

The present invention relates to polyurethane and polyurethane-urea polymers which have shape memory characteristics. The polymers respond to their shape memory when heated in a temperature range of about 20° C. to about 100° C. and are suitable for manufacturing articles, devices and implants requiring shape memory properties. The polymers are particularly useful in biomedical applications.

A shape memory polymer as a cast, moulded, foamed or extruded shape is capable of remembering a basic shape such as plane configuration and dead folds and taking on a second shape when the basic shape is modified[1]. The basic shape can be modified by changing the plane configuration and adding further folds, twists, kinks, bends and/or other three dimensional configurations at a temperature higher than the glass transition point ($T_g$) of the polymer, but lower than the moulding temperature. The modified shape is typically set when the polymer is cooled in the modified state to a temperature lower than the glass transition temperature. The method of utilising the shape memory is by heating the modified shape to a temperature higher than the glass transition temperature thereby restoring the original shape. Polymers with such characteristics combined with biostability would find many applications in the fabrication of various medical devices. The device shape can be optimised depending on the location site, for example, the shape could be modified by coiling or collapsing and subsequent cooling to a temperature below the glass transition temperature to freeze the modified shape. Thermally triggered shape memory could then occur thereby returning the device to its original shape to enable fixing or anchoring to the location site. Medical devices which would benefit from such shape memory characteristics include bone suture anchors, vascular, esophageal and bilial stents and cochlear implantations.

Segmented copolymers such as thermoplastic polyurethanes usually exhibit shape memory characteristics if formulated such that the glass transition temperature of one segment falls within a useful temperature range of about 25° C. to about 60° C. Such polyurethanes are generally prepared from polyester or polyether macrodiols, aromatic diisocyanates and chain extenders[1,2,3].

The shape memory polyurethane compositions disclosed in U.S. Pat. Nos. 5,049,591 and 5,139,832 are formulated with conventional reagents used in the art of polyurethane manufacture and hence are prone to degradation, particularly under the oxidative and hydrolytic conditions present in biological environments.

The stability of such compositions in long term implant applications is expected to be very poor since commercial polyurethanes such as Estane are based on degradation-prone[4,5] polytetramethylene oxide (PTMO), 4,4,'-diphenylmethane diisocyanate and 1,4-butanediol. Similarly, polycarbonate macrodiol based shape memory polyurethanes are expected to have very poor hydrolytic resistance and be unsuitable for long term medical implants[6]. These commercial polyurethanes often also contain small amounts of low molecular weight residues and additives that leach out of the polyurethane and cause undesirable biological responses.

U.S. Pat. No. 5,814,705 discloses shape memory compositions based on blends of commercial polyurethanes such as Estane with other block copolymers. The compatibility of the component polymers may not be sufficient to have a homogeneous shape memory polymer composition. Such compositions, particularly in long term use, may lead to poor performance due to a phase separation of the component polymers.

A range of biostable polyurethanes are disclosed in International Patent Publication Nos. WO98/13405 and WO99/03863 and U.S. Pat. No. 5,393,858. We have found that by proper choice of components and the relative amounts of the hard and soft segments that biostable polyurethanes can be formulated to have one glass transition temperature in a temperature range of about 20° C. to about 100° C. Such polyurethanes therefore possess both the properties of biostability, compatibility and shape memory which enable them to be used in the manufacture of medical articles, devices and implants.

According to the present invention there is provided a shape memory polyurethane or polyurethane-urea polymer including a reaction product of (a), (b) and (c) as set out under (A) below, a reaction product of (b) and (c) as set out under (B) below or a reaction product of (b) and (d) as set out under (C) below:

(A) (a) silicon-based macrodiol, silicon-based macrodiamine and/or polyethers of the formula (I):

$$A-[(CH_2)_m-O]_n-(CH_2)_m-A' \quad \quad (I)$$

wherein

A and A' are endcapping groups;

m is an integer of 6 or more; and n is an integer of 1 or greater;

(b) a diisocyanate; and (c) a chain extender, (B) (b) a diisocyanate;

(c) a chain extender; and no soft segment; or (C) (b) a diisocyanate; and (d) a silicon-containing chain extender, said polymer having a glass transition temperature which enables the polymer to be transformed from its original shape into a first shape at a temperature higher than the glass transition temperature and maintained in said first shape when the polymer is cooled to a temperature lower than the glass transition temperature, said polymer then being capable of resuming its original shape on heating to a temperature higher than the glass transition temperature.

The term "endcapping group" is used herein in its broadest sense and includes reactive functional groups or groups containing reactive functional groups. Suitable examples of reactive functional groups are alcohols, carboxylic acids, aldehydes, ketones, esters, acid halides, acid anhydrides, amines, imines, thio, thioesters, sulphonic acid and expoxides. Preferably the reactive functional group is an alcohol or an amine, more preferably an alcohol.

Further according to the present invention there is provided a shape memory polyurethane or polyurethane-urea composition which includes at least one of the shape memory polyurethane or polyurethane-urea polymers defined above and optionally another material.

Component (a) is preferably a combination of at least two macrodiols, at least two macrodiamines or at least one macrodiol and at least one macrodiamine. Shape memory polymers in which component (a) is a combination of at least two macrodiols or at least one macrodiol and at least one macrodiamine preferably have greater than about 50% silicon-based macrodiol, in particular greater than about 70% as such polymers possess good biostability. A suitable molecular weight range of component (a) is about 300 to about 2000, more preferably about 300 to about 700.

The silicon-based macrodiol or macrodiamine may be a polysilane, polysiloxane, amino-terminated polysiloxane or a silicon-based polycarbonate.

The polysiloxane or amino-terminated polysiloxane may be represented by the formula (II):

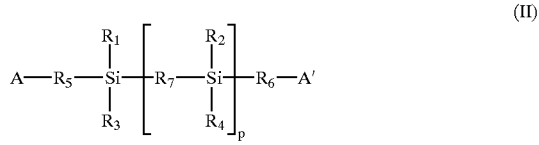

(II)

wherein

A and A' are as defined above;

$R_1$, $R_2$, $R_3$, $R_4$, $R_5$ and $R_6$ are the same or different and selected from hydrogen or an optionally substituted straight chain, branched or cyclic, saturated or unsaturated hydrocarbon radical;

$R_7$ is a divalent linking group or an optionally substituted straight chain, branched or cyclic, saturated or unsaturated hydrocarbon radical; and p is an integer of 1 or greater.

The hydrocarbon radical for substituents R, $R_1$, $R_2$, $R_3$ and $R_4$ may include alkyl, alkenyl, alkynyl, aryl or heterocyclyl radicals. It will be appreciated that the equivalent radicals may be used for substituents $R_5$, $R_6$ and $R_7$ except that the reference to alkyl, alkenyl and alkynyl should be to alkylene, alkenylene and alkynylene, respectively. In order to avoid repetition, only detailed definitions of alkyl, alkenyl and alkynyl are provided hereinafter.

The term "alkyl" denotes straight chain, branched or mono- or poly-cyclic alkyl, preferably $C_{1-12}$ alkyl or cycloalkyl. Examples of straight chain and branched alkyl include methyl, ethyl, propyl, isopropyl, butyl, isobutyl, sec-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-,4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl, cyclodecyl and the like.

The term "alkenyl" denotes groups formed from straight chain, branched or mono- or poly-cyclic alkenes including ethylenically mono- or poly-unsaturated alkyl or cycloalkyl groups as defined above, preferably $C_{2-12}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-(cycloocta-tetraenyl) and the like.

The term "alkynyl" denotes groups formed from straight chain, branched, or mono- or poly-cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl", denotes mono- or poly-cyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6 membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

Suitable divalent linking groups for $R_7$ include O, S and NR wherein R is hydrogen or an optionally substituted straight chain, branched or cyclic, saturated or unsaturated hydrocarbon radical.

Preferred polysiloxanes are polysiloxane macrodiols which are polymers of the formula (II) wherein R and R' are hydroxy and include those represented by the formula (III):

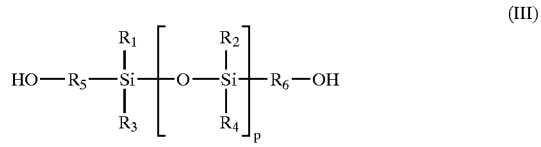

wherein $R_1$ to $R_6$ and p are as defined in formula (II) above.

A preferred polysiloxane is PDMS which is a compound of formula (III) wherein $R_1$ to $R_4$ are methyl and $R_5$ and $R_6$ are as defined above. Preferably $R_5$ and $R_6$ are the same or different and selected from propylene, butylene, pentylene, hexylene, ethoxypropyl ($-CH_2CH_2OCH_2CH_2CH_2-$), propoxypropyl and butoxypropyl.

The polysiloxane macrodiols may be obtained as commercially available products such as X-22-160AS from Shin Etsu in Japan or prepared according to known procedures. The preferred molecular weight range of the polysiloxane macrodiol is about 200 to about 6000, more preferably about 500 to about 2000.

Other preferred polysiloxanes are polysiloxane macrodiamines which are polymers of the formula (II) wherein A is $NH_2$, such as, for example, amino-terminated PDMS.

Suitable silicon-based polycarbonates include those described in our International Patent Publication No. WO98/54242, the entire content of which is incorporated herein by reference.

A preferred silicon-based polycarbonate has the formula (IV):

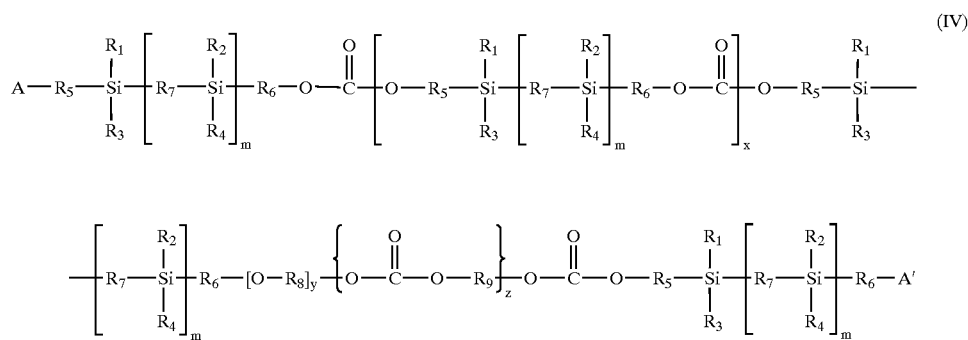

wherein $R_1$, $R_2$, $R_3$, $R_4$, $R_5$, $R_6$ and $R_7$ are as defined in formula (I) above;

$R_8$ and $R_9$ are same or different and selected from hydrogen or an optionally substituted straight chain, branched or cyclic, saturated or unsaturated hydrocarbon radical;

A and A' are as defined in formula (I) above;

m, y and z are integers of 0 or more; and x is an integer of 0 or more.

Preferably z is an integer of 0 to about 50 and x is an integer of 1 to about 50. Suitable values for m include 0 to about 20, more preferably 0 to about 10. Preferred values for y are 0 to about 10, more preferably 0 to about 2.

A preferred polycarbonate is a compound of the formula (IV) wherein the endcapping group is a hydroxy which is a polycarbonate macrodiol of the formula (IVa):

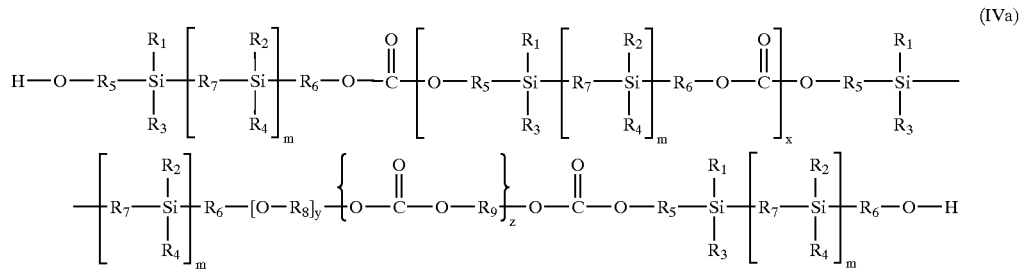

(IVa)

wherein
R₁ to R₉, m, y, x and z are as defined in formula (IV) above.

Particularly preferred polycarbonate macrodiols are compounds of the formula (IVa) wherein $R_1$, $R_2$, $R_3$ and $R_4$ are methyl, $R_8$ is ethyl, $R_9$ is hexyl, $R_5$ and $R_6$ are propyl or $R_4$ butyl and $R_7$ is 0 or —CH₂—CH₂—, more preferably $R_5$ and $R_6$ are propyl when $R_7$ is 0 and $R_5$ and $R_6$ are butyl when $R_7$ is —CH₂—CH₂—. The preferred molecular weight range of the polycarbonate macrodiol is about 400 to about 5000, more preferably about 400 to about 2000.

Suitable polyethers include polyether macrodiols represented by the formula (V):

wherein
m is as defined in formula (I) above, preferably 6 to 18; and
n is as defined in formula (I) above, preferably 1 to 50.

Polyether macrodiols of formula (V) wherein m is 6 or higher such as poly(hexamethyleneoxide) (PHMO), poly (heptamethyleneoxide), poly(octamethylene oxide) (POMO) and poly(decamethylene oxide) (PDMO) are preferred over the conventional PTMO. PHMO and PDMO are particularly preferred due to their relatively high glass transition temperatures.

The polyether macrodiols may be prepared by the procedure described by Gunatillake et al[6]. The preferred molecular weight range of the polyether macrodiol is about 300 to about 2000, more preferably about 300 to about 700.

In a particularly preferred embodiment, component (a) is a combination of PDMS or amino-terminated PDMS with another polymer falling within the scope of component (a), for example, a polyether of the formula (I) such as PHMO or a silicon-based polycarbonate such as siloxy carbonate.

The diisocyanates may be aliphatic or aromatic diisocyanates such as, for example 4,4'-diphenylmethane diisocyanate (MDI), methylene biscyclohexyl diisocyanate (H₁₂MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI). MDI is particularly preferred.

The chain extender may be selected from diol or diamine chain extenders. Examples of diol chain extenders include 1,4-butanediol, 1,6-hexanediol, 1,8-octanediol, 1,9-nonanediol, 1,10-decanediol, 1,12-dodecanediol, 1,4-cyclohexanediol, 1,4-cyclohexanedimethanol, p-xyleneglycol, 1,3-bis(4-hydroxybutyl) tetramethyldisiloxane, 1,3-bis(6-hydroxyethoxypropyl) tetramethyldisiloxane and 1,4-bis(2-hydroxyethoxy) benzene. Suitable diamine chain extenders include 1,2-ethylenediamine, 1,3-propanediamine, 1,4-butanediamine, 1,3-bis(3-aminopropyl)tetramethyldisiloxane, 1,3-bis(4-aminobutyl)tetramethyldisiloxane and 1,6-hexanediamine.

The chain extender may also be a silicon-containing chain extender of the type described in our International Patent Publication No. W099/03863, the entire contents of which are incorporated herein by reference. Such chain extenders include a silicon-containing diol of the formula (VI):

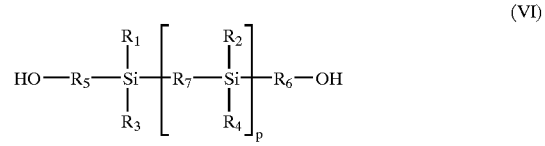

(VI)

wherein
$R_1$, $R_2$, $R_3$, $R_4$, $R_5$, $R_6$ and $R_7$ are as defined in formula (II) above; and
q is 0 or greater, preferably 2 or less.

Component (a) of the polymer generally forms the soft segment of the polyurethane or polyurethane-urea and provides the low glass transition temperature. The high glass transition temperature is provided by the hard segment components (b) and (c).

Preferably, the amount of hard segment in the polymer of the present invention is about 30 to about 100 wt %, more preferably about 50 to about 80 wt %, most preferably about 60 to about 70 wt %. However, it will be appreciated that this amount is dependent on the type of soft segment polymer used, in particular the molecular weight of this polymer. For example, when the molecular weight of the soft segment polymer is about 500, then a 55 to 60 wt % hard segment is preferred. If the molecular weight of the soft segment polymer is about 1000, then a 45 to 55 wt % hard segment is preferred.

For most applications, it is preferred that the shore hardness of the polymer below the glass transition temperature is in the range of about 82D to about 50D, while the hardness above the glass transition temperature is in the range of about 20D to about 30D. The glass transition temperatures of the polymers and compositions of the present invention are generally in the range of about 20° C. to about 100° C., preferably about 20 to about 60° C. However, in some applications such as biotechnological applications, it may be advantageous for the glass transition temperature to be sub ambient i.e., below about 20° C.

It will be appreciated that the shape memory compositions of the present invention may include a blend of two or more of the shape memory polyurethane or polyurethane-urea polymers defined above or at least one shape memory polyurethane or polyurethane-urea polymer defined above in combination with another material. The other material will preferably be of any suitable known type which does not substantially effect the shape memory and/or biostability properties of the polymers of the present invention and may include polymeric and non-polymeric materials.

Examples of polymeric materials include conventional polyurethanes such as PELETHANE™, ESTANE™, CARBOTHANE™, CORETHANE™ and CHRONOFLEX™; shape memory polyurethanes such as those disclosed in U.S. Pat. Nos. 5,145,935 and 5,135,786 and available from Mitsubishi Heavy Industries Ltd (distributed by Memry Corporation in the United States of America; polyolefins such as polyethylene, polypropylene, ethylene propylene copolymers, metallocene polymers, ethylene vinylacetate copolymers and polyvinyl chloride; polyamides; and liquid crystalline polymers such as those available from Eastman Kodak (XG7), Mitsubishi Chemical Industry (Novaculates) and Idemitsu Petrochemical Industry (Idemitsu LCP and Unitika (Lodrum LC). Such polymeric materials generally blend well with the shape memory polymers of the present invention which usually contain high levels of polysiloxane segments.

Each of the polymers forming the shape memory composition preferably have different glass transition temperatures and/or different amounts of hard segment component. Suitable compositions may include a first polymer with a low glass transition temperature, preferably below about ambient temperature and a second polymer with a glass transition temperature above the ambient temperature, more preferably above about 50° C. The two polymers can be blended in proportions such that the final blend will have a glass transition temperature in the preferred range of about 20° C. to about 60° C. Generally the glass transition temperature of the composition is intermediate to those of the two polymers.

Alternatively, the composition may include a first polymer having a high percentage of hard segment component, for example, above about 70 wt %, more preferably above about 90%. Particularly preferred examples of such polymers are the non-elastomeric polyurethane or polyurethane-urea polymers disclosed in International Patent Application No. PCT/AU99/00236. This first polymer can be blended with a second polymer having a lower percentage of hard segment, for example, about 30 to about 60 wt %, more preferably about 40 to about 50 wt %. Examples of suitable polymeric blends include a combination of an elastomeric and a non-elastomeric polyurethane or polyurethane-urea polymer. The term "non-elastomeric" refers to polyurethanes having a % elongation of up to about 200% generally up to about 100%. This technique allows a composition having a softening temperature appropriate for the application to be prepared.

The shape memory polymers and compositions of the present invention may be prepared by any technique familiar to those skilled in the manufacture of polyurethanes. These include one or two-step bulk or solution polymerisation procedures. The polymerisation can be carried out in conventional apparatus or within the confines of a reactive extruder continuous injection moulding or mixing machines.

In a one-step bulk polymerisation procedure the appropriate amount of component (a) is mixed with the chain extender first at temperatures in the range of about 45 to about 100° C., more preferably about 60 to about 80° C. If desired a catalyst such as stanneous octoate or dibutyltin dilaurate at a level of about 0.001 to about 0.5 wt % based on the weight of the total ingredients may be added to the initial mixture. Molten diisocyanate is then added and mixed thoroughly to give a homogeneous polymer liquid and cured by pouring the liquid polymer into Teflon-coated trays and heating in an oven to about 100° C.

The shape memory polymers can also be prepared by a two-step method where a prepolymer is prepared by reacting component (a) with a diisocyanate. The prepolymer is then reacted with a suitable chain extender.

The polymers and compositions of the present invention are particularly useful in preparing materials having good mechanical properties, more specifically biomaterials as a consequence of their biostability or improved resistance to degradation and their shape memory properties.

According to another aspect of the present invention there is provided a material having improved mechanical properties, clarity, processability, biostability and/or degradation resistance including the polymer or composition defined above.

The present invention also provides use of the polymer or composition defined above as a material having improved mechanical properties, clarity, processability, biostability and/or degradation resistance.

The present invention further provides the polymer or composition defined above when used as a material having improved mechanical properties, clarity, processability, biostability and/or degradation resistance.

The mechanical properties which are improved include tensile strength, tear strength, flex fatigue resistance, abrasion resistance, Durometer hardness, flexural modulus and related measures of flexibility or elasticity.

The improved resistance to degradation includes resistance to free radical, oxidative, enzymatic and/or hydrolytic processes and to degradation when implanted as a biomaterial.

The improved processability includes ease of processing by casting such as solvent casting and by thermal means such as extrusion and injection molding, for example, low tackiness after extrusion and relative freedom from gels.

The term "biostability" is used herein in its broadest sense and refers to a stability when in contact with cells and/or bodily fluids of living animals or humans.

There is also provided a biostable material which includes the polymer or composition defined above.

There is further provided a degradation resistant material which includes the polymer or composition defined above.

The polymer or composition of the present invention should also have a good compatibility and stability in biological environments, particularly when implanted in vivo for extended periods of time.

According to another aspect of the present invention there is provided an in vivo degradation resistant or biostable material which includes the polymer or composition defined above.

The polymer or composition may also be used as a biomaterial. The term "biomaterial" is used herein in its broadest sense and refers to a material which is used in situations where it comes into contact with the cells and/or bodily fluids of living animals or humans.

The polymer or composition is therefore useful in manufacturing medical devices, articles or implants.

Thus, the present invention still further provides medical devices, articles or implants which are composed wholly or partly of the polymer or composition defined above.

The medical devices, articles or implants may include catheters; stylets; bone suture anchors; vascular, oesophageal and bilial stents; cochlear implants; reconstructive facial surgery; controlled drug release devices; components in key hole surgery; biosensors; membranes for cell encapsulations; medical guidewires; medical guidepins; cannularizations; pacemakers, defibrillators and neurostimulators and their respective electrode leads; ventricular assist devices; orthopaedic joints or parts thereof including spinal discs and small joints; cranioplasty plates; intraoccular lenses; urological stents and other urological devices; stent/graft devices; device joining/extending/repair sleeves; heart valves; vein grafts; vascular access ports; vascular shunts; blood purification devices; casts for broken limbs; vein valve, angioplasty, electrophysiology and cardiac output catheters; and tools and accessories for insertion of medical devices, infusion and flow control devices.

As the polymers and compositions of the present invention may be designed so that they are rigid at ambient temperature but soften around the body temperature they have many applications in the construction of medical articles, devices and implants. For example, intravenous catheters made from such materials could be inserted initially in the vein due to the high flexural modulus of the material, but would then soften once inside the blood vessel. Furthermore, catheters may be modified to a predetermined shape for ease of directing to a target area or modified in such a way to have sections with different softening temperatures, for ease of guidance of the device to a specific location.

It will be appreciated that polymers and compositions having properties optimised for use in the construction of various medical devices, articles or implants and possessing shape memory characteristics will also have other non-medical applications. Such applications may include toys and toy components, shape memory films, pipe couplings, electrical connectors, zero-insertion force connectors, Robotics, Aerospace actuators, dynamic displays, flow control devices, sporting goods and components thereof, body-conforming devices, temperature control devices, safety release devices and heat shrink insulation.

Thus, the present invention extends to the use of the polymer or composition defined above in the manufacture of devices or articles.

The present invention also provides devices or articles which are composed wholly or partly of the polymer or composition as defined above.

The invention will now be described with reference to the following non-limiting examples.

EXAMPLE 1

Poly(hexamethylene oxide) (PHMO) (MW 489.7) was prepared according to a method described by Gunatillake et al[7] and U.S. Pat. No. 5,403,912 and dried at 130° C. under vacuum for 4 h. A shape memory polyurethane composition from PENO was prepared according to a one-step bulk polymerisation as described below.

PHMO (35.00 g) and 1,4-butanediol (BDO) (12.06 g) were weighed in to a 500 mL polypropylene beaker and the contents warmed to 70° C. Molten MDI (52.93 g) was weighed into a 100 mL, wet-tared polypropylene beaker and added to the PHMO/BDO mixture quickly with stirring. The mixture was stirred for about 30 sec and the contents poured onto a Teflon-coated metal pan. The polyurethane was cured at 100° C. for 4 h under nitrogen. The resulting polyurethane was clear and transparent. The specimens for various tests were prepared by compression molding at a temperature of 200° C. and injection moulding.

Dynamical Mechanical Thermal Analysis, DMTA (Rheometrics MkIIe) was performed on 40 mm ×10 mm ×1 mm compression moulded samples in single cantilever bending mode at Htz over a temperature range of 30° C. to 90° C. at a ramp rate of 2° C./min. The onset of the change in the bending modulus was at 37° C. (1100±50 MPa bending mod) and the endset of change in the bending modulus was 56° C. (50±20 MPa bending modulus).

The shape memory characteristics of the polyurethane composition were demonstrated as follows. An injection moulded flat, 2.5 mm thick plaque of the polyurethane and a compression moulded flat thin film (0.1 mm thick) were folded 180° at 55° C. and cooled to 20° C. so that the plaque and thin film were locked into a 180° folded configuration. The folded plaque and the thin film were stored for 72 hours without any configurational change and then subsequently heated in water to 55° C. at which point the folded thin film very quickly (<1 sec) returned to its original flat configuration and the thicker plaque returned also to its original flat configuration but more slowly (ca. 20 secs).

A reverse experiment was also performed whereby permanent 180° folds were placed in the samples by compressing between flat plates heated to 150° C. The thick and thin samples were then heated to 55° C. and the 180° fold undone to 0°, this unfolding being locked in by cooling to 20° C. The samples were stored at ambient temperature for 72 hours in the modified (unfolded) shape with no observable configuration changes. The samples were subsequently heated in water at 55° C. causing the original 180° fold to reform in similar times to those observed in the previous experiment.

EXAMPLE 2

A polyurethane based on PHMO with a molecular weight of 398.0 was prepared using a procedure similar to that described in Example 1. PHMO (32.00 g) and 1,4-butanediol (12.67 g) was weighed into a 500 mL polypropylene beaker and the contents warmed to 70° C. Molten MDI (55.33 g) was weighed into a 100 mL wet-tared polypropylene beaker and added to the PHNO quickly with stirring. The mixture was stirred for about 30 sec and the contents poured onto a Teflon-coated metal pan. The polyurethane was cured at 100° C. for 4 h under nitrogen. The resulting polyurethane was clear and transparent. The test specimens for various tests were prepared by compression moulding at a temperature of 200° C. and injection moulding.

The onset of the change in the bending modulus was at 46° C. (1050±50 MPa bending mod) and the endset of change in the bending modulus was 60° C. (50±20 MPa bending mod) as determined by DMTA analysis. The shape memory characteristics of the composition was similar to that of the composition of Example 1.

EXAMPLE 3

This example illustrates the preparation of shape memory polyurethane compositions with desired glass transition temperatures in the 20° C. to 100° C. range by solvent blending of two polyurethane compositions, one with a low flexural modulus (approximately in the range of about 15 to about 100 MPa range) and the other with a high flexural modulus (>500MPa).

The low modulus polyurethane composition was prepared by reacting bis(6-hydroxyethoxypropyl) polydimethylsiloxane (48.00 g, MW 940.3), poly(hexamethylene oxide) (12.00 g, MW 700.2), 1,4-butanediol (5.80 g) and MDI (34.19 g) according to a one-step polymerisation procedure. The flexural modulus of the polyurethane was 30 MPa.

The high modulus polyurethane composition was prepared by reacting 1,4-cyclohexanedimethanol (25.27 g), 1,3bis(4-hydroxybutyl)-1,1,3,3-tetramethyldisiloxane (16.27 g) and MDI (58.46 g) according to a one-step bulk polymerisation. The flexural modulus of the polyurethane was 1770 MPa.

Differential scanning calorimetry (at a ramp rate of 10° C./min) demonstrated the presence of glass transition change onset at 91.2° C. and an endset at 106.7° C. with a Cp of 0.28J.g$^{-1}$.° C.$^{-1}$. This high modulus composition exhibited shape memory characteristics. A compression moulded thin plaque (0.1 mm) was folded at 110° C. and immediately cooled to ambient temperature to preserve the fold. It was subsequently heated to 110° C. resulting in a reversal of the shape to the original.

The high modulus and low modulus polyurethanes were blended by mixing 7.5 g and 2.5 g, respectively and dissolving the blend in N,N-dimethylformamide to give a 20 wt % solution. A thin film of the blend was prepared by solvent casting. The polymer solution was poured onto a Petrie Dish to form a 5 mm thick layer and the solvent evaporated in a nitrogen circulating oven over a period of 48 h. DSC analysis of the dried film showed a glass transition onset temperature of 45.6° C. and an end set at 49.5   C.

A thin film (0.3 mm) of the blend was folded by 180° by heating to a temperature above 50° C. and the folded shape fixed by cooling to room temperature. The folded shape reverted to the original shape when it was heated to 50° C. exhibiting the shape memory characteristics of the blended polyurethane.

EXAMPLE 4

A polyurethane composition based on 1,3-bis(4-hydroxybutyl)tetramethyldisiloxane (BHTD) and MDI was prepared.

BHTD (Silar Laboratories, 55.68 g) was added to molten (45° C.) MDI (50.00 g) and thoroughly mixed until a clear and homogenous solution was obtained. This required about 3 min of stirring. The viscous polymer was then poured onto a Teflon-coated metal tray and cured at 100° C. for 4 h in an oven under nitrogen. The resulting polymer was clear and transparent. The cured polyurethane was compression moulded at 200° C. to a 1 mm thick plaque. The materials exhibited a shore hardness of 75D, ultimate tensile strength of 60 MPa, and flexural modulus of 1795 MPa.

The onset of glass transition temperature was 30° C. and the polyurethane remained rigid below 30° C. and softened at body temperature (37° C.).

EXAMPLE 5

This example illustrates the preparation of a polyurethane using a low molecular weight siloxane macrodiol such that the polyurethane composition has a glass transition temperature close to the body temperature. The polyurethane was prepared by reacting 4,4'-methylenediphenyl diisocyanate (MDI, Orica), α, β-bis (6-hydroxyethoxypropyl)-polydimethylsiloxane (PDMS MW 595) and 1,4-cyclohexanedimethanol (Aldrich). PDMS with a molecular weight of 595 was obtained by distilling Shin-Etsu product X-22-160AS (Lot No. 803037) using a wiped-film evaporator.

PDMS was degassed at ambient temperature under vacuum (0.1 torr) for 4 h prior to polymerisation and CHDM (Aldrich) was melted at 60° C. and degassed under vacuum (0.1 torr) for 1 h.

Degassed PDMS (5.94 g) was added to molten (50° C.) MDI (5.00 g) in a polypropylene beaker and stirred rapidly until the solution turned clear followed by adding CHDM (1.44 g). After stirring the mixture for further 35 sec, the viscous polymer was poured onto a Teflon-coated pan and cured at 100° C. for 6 h under nitrogen. Tensile properties were measured on a compression moulded sheet. DSC analysis was carried out to determine the glass transition temperature of the polyurethane. The polyurethane exhibited an ultimate tensile strength of 23.3 +MPa, elongation at break of 97±8% and a Young's modulus of 201±65. The DSC results showed the onset of glass transition to be 26° C., mid point at 34° C. and end at 42° C. The polyurethane showed shape memory properties when tested using the procedure described in Example 3.

EXAMPLE 6

This example illustrates the preparation of shape memory polyurethanes by blending commercial polyurethanes and a high modulus polyurethane with a glass transition temperature of about 100° C. PELLETHANE™ 2363-80A and CORETHANE™ AW 80 were used as examples of commercial polyurethanes.

The high modulus polyurethane was prepared using the following procedure. Molten (50° C.) MDI (500.00 g) was weighed into a 2 L polypropylene beaker. The chain extenders BHTD (139.11 g) and CHDM (216.08 g) were weighed separately into two wet-tared polypropylene beakers. BHTD was added to MDI and stirred for about 45 seconds followed by molten (80° C) CHDM. Stirring was continued for another 20 to 25 sec and the viscous polymer was immediately stirred into a Teflon-coated tray. The tray containing the polymer was kept under nitrogen at ambient temperature for about 45 min and cured at 100° C. for 4 h.

Two compositions were prepared by blending the high modulus polyurethane with CORETHANE™ and PELLETHANE™, respectively. Composition 1 was prepared by dissolving 7.5 g of the high modulus polyurethane with 2.5 g of CORETANE™ in 40 mL of dimethyl acetamide. The mixture was cast into a thin film by pouring the solution into a Petrie dish and evaporating the solvent in a nitrogen circulating oven at 70° C. for 48 h. Similarly Composition-2 was prepared by dissolving 2.5 g of PELLETRANE™ and 7.5 g of the high modulus polyurethane in dimethylacetamide and casting a thin film of the composition.

The tensile properties and glass transition temperature of the two compositions were determined and the results are summarised in Table 1 below. The two compositions showed shape memory properties when tested using the procedure described in Example 3.

TABLE 1

Tensile properties and glass transition temperatures of the polyurethane compositions prepared in Example 6.

| Composition | Elon. % | UTS MPa | YM MPa | Tg (° C.)Onset | Mid point | Endpoint |
|---|---|---|---|---|---|---|
| Composition 1 | 13 | 41.5 | 648 | 39.8 | 43.2 | 46.7 |
| Composition 2 | 13 | 28.0 | 280 | 44.6 | 48.3 | 52.0 |

References

1. J. R. Lin and L. W. Chen, *J Appl. Polym. Sci.,* 69, 1563 (1998).
2. S. Hayashi, S. Kondo and K. Kawamura, 34$^{th}$ Annual Polyurethanes Technical Marketing Conf, p. 605 (1992).

3. T. Takahashi, N. Hayashi and S. Hayashi, *J. Appl. Polym. Sci.,* 60, 1061 (1996).
4. S. J. McCarthy, G. F. Meijs, N. Mitchell, P. A. Gunatillake, G. Heath, A. Brandwood and K. Schindhelm, *Biomaterials,* 18, 1387 (1997).
5. L. Pinchuck, *J. Biomater. Sci. Edn.* Vol 3 (3), 225 (1994).
6. Y. W. Tang, J. P. Santerre, R. S. Labow, I. Revenko and M. A. Sing, $25^{th}$ *Annual Meeting, Society for Biomaterials.* Rhode Island, USA, p 58 (1999).
7. P. A. Gunatillake, G. F. Meijs, R. C. Chatelier, D. M. McIntosh, and E. Rizzardo *Polym. Znt.* Vol 27, pp 275 (1992).

What is claimed is:

1. A biostable shape memory polyurethane or polyurethane-urea polymer comprising a reaction product of (a), (b) and (c) as set out below:
   (a) a silicon-based macrodiol and a polyether of formula (I) below; a silicon-based macrodiamine and a polyether of formula (I) below; or a silicon-based microdiol, a silicon-based macrodiamine and polyether of formula (I):

(I)

wherein
   A and A' are endcapping groups;
   m is an integer of 6 or more; and
   n is an integer of 1 or greater,
   (b) a diisocyanate; and
   (c) a chain extender,
   wherein the silicon-based macrodiol and macrodiamine are silicon-based polycarbonates having the formula (IV):

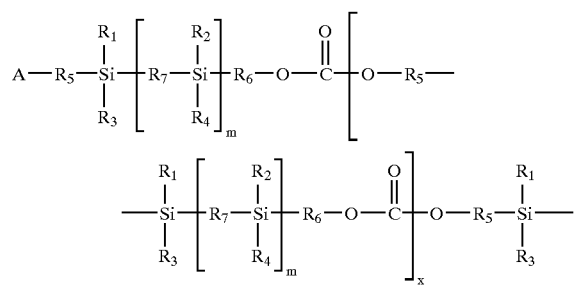

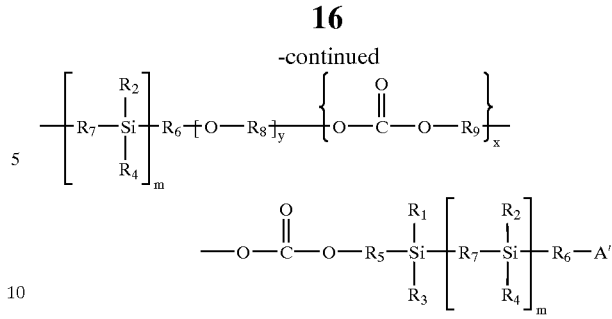

wherein:
   $R_1$, $R_2$, $R_3$ and $R_4$ are the same or different and selected from hydrogen or an optionally substituted straight chain, branched chain and cyclic, saturated or unsaturated hydrocarbon radical;
   $R_5$, $R_6$, $R_8$ and $R_9$ are the same or different and selected from an optionally substituted straight chain, branched chain and cyclic, saturated or unsaturated divalent hydrocarbon radical;
   $R_7$ is a divalent linking group or an optionally substituted straight chain, branched chain or cyclic, saturated or unsaturated hydrocarbon radical;
   A and A' are as defined in formula (I);
   m, y and z are integers of 0 or more; and
   x is an integer of 0 or more
   said polymer having a glass transition temperature which enables the polymer to be transformed from its original shape into a first shape at a temperature higher than the glass transition temperature and maintained in said first shape when the polymer is cooled to a temperature lower than the glass transition temperature, said polymer then being capable of resuming its original shape on heating to a temperature higher than the glass transition temperature.

2. A shape memory polyurethane or polyurethane-urea polymer according to claim 1, wherein z is an integer of 0 to about 50, x is an integer of 1 to about 50, m is an integer of 0 to about 20 and y is an integer of 0 to about 10.

3. A shape memory polyurethane or polyurethane-urea polymer according to claim 1, wherein the silicon-based polycarbonate is a compound of the formula (IV) wherein the endcapping group is a hydroxy which is a polycarbonate macrodiol of the formula (IVa):

(IVa)

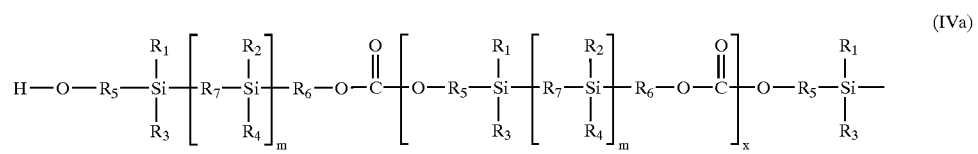

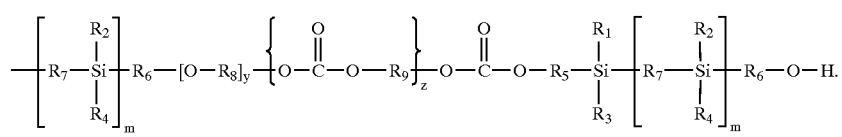

4. A shape memory polyurethane or polyurethane-urea polymer according to claim 3, wherein the polycarbonate macrodiol is a compound of the formula (IVa) wherein $R_1$, $R_2$, $R_3$ and $R_4$ are methyl, $R_8$ is ethyl, $R_9$ is hexyl, $R_5$ and $R_6$ are propyl or butyl and $R_7$ is O or —$CH_2$—$CH_2$—.

5. A shape memory polyurethane or polyurethane-urea polymer according to claim 4 wherein $R_5$ and $R_6$ are propyl when $R_7$ is O and $R_5$ and $R_6$ are butyl when $R_7$ is —$CH_2$—$CH_2$—.

* * * * *

UNITED STATES PATENT AND TRADEMARK OFFICE
CERTIFICATE OF CORRECTION

PATENT NO.       : 6,858,680 B2
APPLICATION NO.  : 10/054742
DATED            : February 22, 2005
INVENTOR(S)      : Gunatillake et al.

It is certified that error appears in the above-identified patent and that said Letters Patent is hereby corrected as shown below:

On the face page, in field (57), under "Abstract", in column 2, line 5, delete "A and A" and insert -- A and A' --, therefor.

In column 1, line 63, delete "4,4,'-" and insert -- 4,4'- --, therefor.

In column 4, line 30, ""heterocylyl"" delete ",".

In column 11, line 51, delete "PENO" and insert -- PHMO --, therefor.

In column 11, line 65, delete "Mklle" and insert -- Mkllle --, therefor.

In column 12, line 36, delete "PHNO" and insert -- PHMO --, therefor.

In column 14, line 37, delete "CORETANE™" and insert -- CORETHANE™ --, therefor.

In column 14, line 42 – 43, delete "PELLETRANE™" and insert -- PELLETHANE™ --, therefor.

In column 15, line 13, delete "Znt." and insert -- Int. --, therefor.

In column 15, line 22, in Claim 1, after "and" insert -- a --.

UNITED STATES PATENT AND TRADEMARK OFFICE
CERTIFICATE OF CORRECTION

PATENT NO. : 6,858,680 B2
APPLICATION NO. : 10/054742
DATED : February 22, 2005
INVENTOR(S) : Gunatillake et al.

It is certified that error appears in the above-identified patent and that said Letters Patent is hereby corrected as shown below:

In column 16, line 1, In Claim 1, delete " 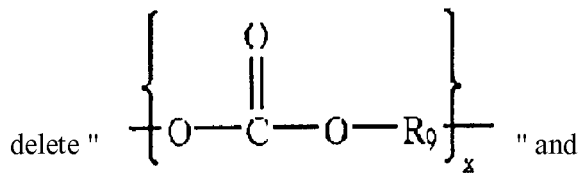 " and insert -- 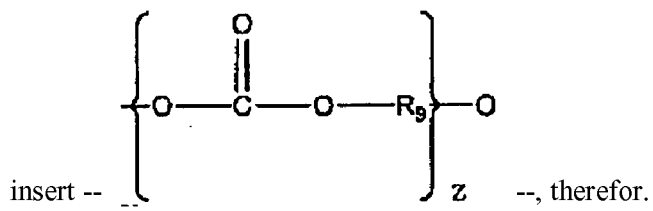 --, therefor.

Signed and Sealed this

Seventeenth Day of October, 2006

JON W. DUDAS
*Director of the United States Patent and Trademark Office*